United States Patent
Ritland

(10) Patent No.: US 8,262,571 B2
(45) Date of Patent: Sep. 11, 2012

(54) INTERMUSCULAR GUIDE FOR RETRACTOR INSERTION AND METHOD OF USE

(76) Inventor: Stephen Ritland, Flagstaff, AZ (US)

( * ) Notice: Subject to any disclaimer, the term of this patent is extended or adjusted under 35 U.S.C. 154(b) by 482 days.

(21) Appl. No.: 10/853,623

(22) Filed: May 24, 2004

(65) Prior Publication Data

US 2004/0254428 A1 Dec. 16, 2004

Related U.S. Application Data

(60) Provisional application No. 60/472,978, filed on May 22, 2003.

(51) Int. Cl.
*A61B 1/32* (2006.01)
(52) U.S. Cl. .................................................... 600/220
(58) Field of Classification Search .............. 600/220, 600/201, 203, 204, 205, 210, 218, 219, 221, 600/226, 239, 104, 114, 190; 606/90, 99, 606/104, 205, 206, 207, 208; D24/135
See application file for complete search history.

(56) References Cited

U.S. PATENT DOCUMENTS

| | | | | |
|---|---|---|---|---|
| 2,191 | A * | 7/1841 | Pitney | 600/221 |
| 569,839 | A | 10/1896 | Roeloffs | |
| 605,652 | A * | 6/1898 | Pitt | 600/223 |
| 1,090,746 | A * | 3/1914 | Nourse | 600/220 |
| 1,097,978 | A * | 5/1914 | Johnson | 606/198 |
| 3,467,079 | A | 9/1969 | James | |
| 3,470,872 | A | 10/1969 | Grieshaber | |
| 3,875,595 | A | 4/1975 | Froning | |
| 3,893,454 | A * | 7/1975 | Hagelin | 600/219 |
| 4,041,939 | A | 8/1977 | Hall | |
| 4,232,660 | A | 11/1980 | Coles | |
| 4,437,458 | A | 3/1984 | Upsher | |
| 4,440,168 | A | 4/1984 | Warren | |
| 4,481,947 | A | 11/1984 | Chester | |
| 4,545,374 | A | 10/1985 | Jacobson | |
| 4,573,448 | A | 3/1986 | Kambin | |
| 4,617,922 | A | 10/1986 | Griggs | |
| 4,620,460 | A | 11/1986 | Gonzales, Jr. | |
| 4,686,972 | A | 8/1987 | Kurland | |
| 4,736,738 | A | 4/1988 | Lipovsek | |
| 4,743,260 | A | 5/1988 | Burton | |
| 4,747,394 | A | 5/1988 | Watanabe | |
| 4,798,111 | A | 1/1989 | Cheeseman | |

(Continued)

FOREIGN PATENT DOCUMENTS

EP 0820731 5/2003

(Continued)

OTHER PUBLICATIONS

Written Opinion for International (PCT) Application No. PCT/US04/16446, mailed Oct. 18, 2005.

(Continued)

*Primary Examiner* — Eduardo C Robert
*Assistant Examiner* — David Comstock
(74) *Attorney, Agent, or Firm* — Bryan Cave LLP

(57) ABSTRACT

A guide is provided for insertion into a surgical incision to create interior access along a preferred plane to an interior surgical site. After inserting the guide into an incision, a retractor or other tool may be inserted though the guide to the interior surgical site. The guide serves as a pathway for the retractor to the interior surgical site of the patient.

23 Claims, 12 Drawing Sheets

U.S. PATENT DOCUMENTS

| | | | |
|---|---|---|---|
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeely | |
| 4,889,112 A * | 12/1989 | Schachner et al. | 128/200.26 |
| 4,974,985 A | 12/1990 | Glatzel | |
| 4,995,875 A | 2/1991 | Coes | |
| 5,002,542 A | 3/1991 | Frigg | |
| 5,002,576 A | 3/1991 | Fuhrmann et al. | |
| 5,018,507 A * | 5/1991 | Montaldi | 600/222 |
| 5,026,373 A | 6/1991 | Ray et al. | |
| 5,030,220 A | 7/1991 | Howland | |
| 5,030,223 A | 7/1991 | Anderson et al. | |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | |
| 5,084,043 A | 1/1992 | Hertzmann | |
| 5,098,435 A | 3/1992 | Stednitz | |
| 5,106,376 A | 4/1992 | Mononen | |
| 5,129,900 A | 7/1992 | Asher et al. | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,165,306 A | 11/1992 | Hellon | |
| 5,195,541 A | 3/1993 | Obenchain | |
| 5,217,007 A * | 6/1993 | Ciaglia | 128/207.29 |
| 5,275,600 A | 1/1994 | Allard et al. | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,306,275 A | 4/1994 | Bryan | |
| 5,306,309 A | 4/1994 | Wagner et al. | |
| 5,312,360 A | 5/1994 | Behl | |
| 5,312,405 A | 5/1994 | Korotko et al. | |
| 5,330,474 A | 7/1994 | Lin | |
| 5,334,194 A | 8/1994 | Mikhail | |
| 5,356,413 A | 10/1994 | Martins et al. | |
| 5,363,841 A | 11/1994 | Coker | |
| 5,397,330 A | 3/1995 | Mikhail | |
| 5,415,661 A | 5/1995 | Holmes | |
| 5,431,639 A | 7/1995 | Shaw | |
| 5,431,651 A | 7/1995 | Goble | |
| D361,381 S | 8/1995 | Koros et al. | |
| 5,439,464 A | 8/1995 | Shapiro | |
| 5,466,238 A | 11/1995 | Lin | |
| 5,472,426 A | 12/1995 | Bonati | |
| 5,474,555 A | 12/1995 | Puno et al. | |
| 5,484,440 A | 1/1996 | Allard | |
| 5,489,274 A | 2/1996 | Chu | |
| 5,489,308 A | 2/1996 | Kuslich et al. | |
| 5,498,262 A | 3/1996 | Bryan | |
| 5,499,983 A | 3/1996 | Hughes | |
| 5,501,684 A | 3/1996 | Schlapfer et al. | |
| 5,512,038 A | 4/1996 | O'Neal et al. | |
| 5,558,622 A | 9/1996 | Greenberg | |
| 5,565,502 A | 10/1996 | Glimcher et al. | |
| 5,569,300 A * | 10/1996 | Redmon | 606/207 |
| 5,584,833 A | 12/1996 | Fournet-Fayard et al. | |
| 5,591,166 A | 1/1997 | Bernhardt et al. | |
| 5,591,235 A | 1/1997 | Kuslich | |
| 5,593,409 A | 1/1997 | Michelson | |
| 5,601,550 A | 2/1997 | Esser | |
| 5,603,714 A | 2/1997 | Kaneda et al. | |
| 5,611,778 A | 3/1997 | Brinon | |
| 5,628,740 A | 5/1997 | Mullane | |
| 5,643,263 A | 7/1997 | Simonson | |
| 5,643,264 A | 7/1997 | Sherman et al. | |
| 5,645,544 A | 7/1997 | Tai et al. | |
| 5,645,599 A | 7/1997 | Samani | |
| 5,683,392 A | 11/1997 | Richelsoph et al. | |
| 5,683,463 A | 11/1997 | Godefroy et al. | |
| 5,687,739 A | 11/1997 | McPherson | |
| 5,690,632 A | 11/1997 | Schwartz et al. | |
| 5,691,397 A | 11/1997 | Glimcher et al. | |
| 5,702,455 A | 12/1997 | Saggar | |
| 5,716,355 A | 2/1998 | Jackson et al. | |
| 5,716,415 A | 2/1998 | Steffee | |
| 5,725,528 A | 3/1998 | Errico et al. | |
| 5,735,850 A | 4/1998 | Baumgartner et al. | |
| 5,735,851 A | 4/1998 | Errico et al. | |
| 5,735,899 A | 4/1998 | Schwartz et al. | |
| 5,743,853 A | 4/1998 | Lauderdale | |
| 5,746,720 A | 5/1998 | Stouder, Jr. | |
| 5,746,741 A | 5/1998 | Kraus et al. | |
| 5,752,957 A | 5/1998 | Ralph et al. | |
| 5,766,221 A | 6/1998 | Benderev et al. | |
| 5,766,253 A | 6/1998 | Brosnahan, III | |
| 5,772,582 A * | 6/1998 | Huttner et al. | 600/219 |
| 5,782,832 A | 7/1998 | Larsen et al. | |
| 5,785,648 A * | 7/1998 | Min | 600/206 |
| 5,785,710 A | 7/1998 | Michelson | |
| 5,785,712 A | 7/1998 | Runciman et al. | |
| 5,792,044 A | 8/1998 | Foley | |
| 5,797,912 A | 8/1998 | Runciman et al. | |
| 5,800,435 A | 9/1998 | Errico et al. | |
| 5,810,816 A | 9/1998 | Roussouly et al. | |
| 5,810,817 A | 9/1998 | Roussouly et al. | |
| D399,955 S | 10/1998 | Koros et al. | |
| 5,816,257 A | 10/1998 | Chin | |
| 5,827,328 A | 10/1998 | Buttermann | |
| 5,836,948 A | 11/1998 | Zucherman et al. | |
| RE36,020 E | 12/1998 | Moore et al. | |
| 5,851,207 A | 12/1998 | Cesarone | |
| 5,860,977 A | 1/1999 | Zucherman et al. | |
| 5,865,847 A | 2/1999 | Kohrs et al. | |
| 5,865,848 A | 2/1999 | Baker | |
| 5,876,404 A | 3/1999 | Zucherman et al. | |
| 5,882,344 A | 3/1999 | Stouder, Jr. | |
| 5,885,285 A | 3/1999 | Simonson | |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | |
| 5,899,901 A | 5/1999 | Middleton | |
| 5,902,231 A | 5/1999 | Foley | |
| 5,902,304 A | 5/1999 | Walker | |
| 5,904,650 A | 5/1999 | Wells | |
| 5,906,616 A | 5/1999 | Pavlov et al. | |
| 5,913,818 A | 6/1999 | Co et al. | |
| 5,928,139 A | 7/1999 | Koros | |
| 5,928,233 A | 7/1999 | Apfelbaum et al. | |
| 5,938,663 A | 8/1999 | Petreto | |
| 5,944,658 A | 8/1999 | Koros et al. | |
| 5,947,965 A | 9/1999 | Bryan | |
| 5,954,635 A | 9/1999 | Foley | |
| 5,954,671 A | 9/1999 | O'Neil | |
| 5,961,516 A | 10/1999 | Graf | |
| 5,967,970 A | 10/1999 | Cowan | |
| 5,968,098 A | 10/1999 | Winslow | |
| 5,971,920 A | 10/1999 | Nagel | |
| 5,976,135 A | 11/1999 | Sherman et al. | |
| 5,976,146 A | 11/1999 | Ogawa | |
| 5,984,924 A | 11/1999 | Asher et al. | |
| 5,996,447 A | 12/1999 | Bayouth | |
| 5,997,539 A | 12/1999 | Errico et al. | |
| 6,004,322 A | 12/1999 | Bernstein | |
| 6,007,487 A | 12/1999 | Foley et al. | |
| 6,010,520 A | 1/2000 | Pattison | |
| 6,017,342 A | 1/2000 | Rinner | |
| 6,027,533 A | 2/2000 | Olerud | |
| 6,045,579 A | 4/2000 | Hochshuler et al. | |
| 6,048,342 A | 4/2000 | Zucherman et al. | |
| 6,050,997 A | 4/2000 | Mullane | |
| 6,063,088 A | 5/2000 | Winslow | |
| 6,068,630 A | 5/2000 | Zucherman et al. | |
| 6,074,390 A | 6/2000 | Zucherman et al. | |
| 6,074,393 A | 6/2000 | Sitoto | |
| 6,080,155 A | 6/2000 | Michelson | |
| 6,080,193 A | 6/2000 | Hochshuler et al. | |
| 6,081,741 A | 6/2000 | Hollis | |
| 6,083,225 A | 7/2000 | Winslow et al. | |

| | | | | | | |
|---|---|---|---|---|---|---|
| 6,090,112 | A | 7/2000 | Zucherman et al. | 6,371,959 B1 | 4/2002 | Trice |
| 6,102,948 | A | 8/2000 | Brosnahan, III | 6,371,968 B1 | 4/2002 | Kogasaka |
| 6,113,602 | A | 9/2000 | Sand | 6,391,058 B1 | 5/2002 | Kuslich et al. |
| 6,117,137 | A | 9/2000 | Halm et al. | 6,395,033 B1 | 5/2002 | Pepper |
| 6,117,174 | A | 9/2000 | Nolan | 6,418,821 B1 | 7/2002 | Yamakawa |
| 6,120,434 | A | 9/2000 | Kimura | 6,425,901 B1 * | 7/2002 | Zhu et al. ............ 606/142 |
| 6,120,506 | A | 9/2000 | Kohrs et al. | 6,428,472 B1 | 8/2002 | Haas |
| 6,123,705 | A | 9/2000 | Michelson | 6,440,169 B1 | 8/2002 | Elberg et al. |
| 6,123,706 | A | 9/2000 | Lange | 6,440,170 B1 | 8/2002 | Jackson |
| 6,132,430 | A | 10/2000 | Wagner | 6,443,953 B1 | 9/2002 | Perra et al. |
| D433,296 | S | 11/2000 | Yamakawa | 6,443,989 B1 | 9/2002 | Jackson |
| 6,146,383 | A | 11/2000 | Studer et al. | 6,461,330 B1 | 10/2002 | Miyagi |
| 6,149,652 | A | 11/2000 | Zucherman et al. | 6,461,359 B1 | 10/2002 | Tribus et al. |
| 6,149,686 | A | 11/2000 | Kuslich et al. | 6,471,724 B2 | 10/2002 | Zdeblick et al. |
| 6,152,871 | A | 11/2000 | Foley | 6,478,798 B1 | 11/2002 | Howland |
| 6,152,926 | A | 11/2000 | Zucherman et al. | D466,766 S | 12/2002 | Marty |
| 6,156,006 | A | 12/2000 | Brosens | 6,506,151 B2 | 1/2003 | Estes |
| 6,156,038 | A | 12/2000 | Zucherman et al. | 6,520,907 B1 | 2/2003 | Foley |
| 6,159,179 | A | 12/2000 | Simonson | 6,524,238 B2 | 2/2003 | Velikaris et al. |
| 6,162,170 | A | 12/2000 | Foley | 6,530,880 B2 | 3/2003 | Pagliuca |
| 6,162,236 | A | 12/2000 | Osada | 6,530,926 B1 | 3/2003 | Davison |
| D436,513 | S | 1/2001 | Yamakawa | 6,540,756 B1 | 4/2003 | Vaughan |
| 6,176,823 | B1 | 1/2001 | Foley | 6,551,320 B2 | 4/2003 | Lieberman |
| 6,176,861 | B1 | 1/2001 | Bernstein et al. | 6,554,831 B1 | 4/2003 | Rivard et al. |
| 6,179,838 | B1 | 1/2001 | Fiz | 6,562,046 B2 | 5/2003 | Sasso |
| D438,074 | S | 2/2001 | Marr | 6,565,569 B1 | 5/2003 | Assaker et al. |
| 6,183,471 | B1 | 2/2001 | Zucherman et al. | 6,569,164 B1 | 5/2003 | Assaker et al. |
| 6,187,005 | B1 | 2/2001 | Brace et al. | 6,576,017 B2 | 6/2003 | Foley et al. |
| 6,190,387 | B1 | 2/2001 | Zucherman et al. | 6,579,292 B2 | 6/2003 | Taylor |
| 6,190,414 | B1 | 2/2001 | Young et al. | 6,585,738 B1 | 7/2003 | Mangione et al. |
| 6,196,696 | B1 | 3/2001 | Shiao | 6,595,993 B2 | 7/2003 | Donno et al. |
| 6,196,969 | B1 | 3/2001 | Bester et al. | 6,610,062 B2 | 8/2003 | Bailey et al. |
| 6,197,002 | B1 | 3/2001 | Peterson | 6,626,904 B1 | 9/2003 | Jammet et al. |
| 6,206,822 | B1 | 3/2001 | Foley | 6,626,906 B1 | 9/2003 | Young |
| 6,206,826 | B1 | 3/2001 | Mathews et al. | 6,648,887 B2 | 11/2003 | Ashman |
| 6,206,885 | B1 | 3/2001 | Ghahremani et al. | 6,671,725 B1 * | 12/2003 | Noel et al. ............ 709/226 |
| 6,206,922 | B1 | 3/2001 | Zdeblick et al. | 6,676,661 B1 | 1/2004 | Martin Benlloch et al. |
| 6,206,923 | B1 | 3/2001 | Boyd et al. | 6,679,833 B2 | 1/2004 | Smith |
| 6,210,413 | B1 | 4/2001 | Justis et al. | 6,682,563 B2 | 1/2004 | Scharf |
| 6,214,004 | B1 | 4/2001 | Coker | 6,685,705 B1 | 2/2004 | Taylor |
| 6,217,509 | B1 | 4/2001 | Foley | 6,692,434 B2 | 2/2004 | Ritland |
| 6,224,597 | B1 | 5/2001 | Coker | 6,736,816 B2 | 5/2004 | Ritland |
| 6,224,608 | B1 | 5/2001 | Ciccolella | 6,743,257 B2 | 6/2004 | Castro |
| 6,224,631 | B1 | 5/2001 | Kohrs | 6,749,613 B1 | 6/2004 | Conchy et al. |
| 6,231,575 | B1 | 5/2001 | Krag | 6,749,614 B2 | 6/2004 | Teitelbaum et al. |
| 6,235,030 | B1 | 5/2001 | Zucherman et al. | 6,752,832 B2 | 6/2004 | Neumann |
| 6,238,397 | B1 | 5/2001 | Zucherman et al. | 6,761,719 B2 | 7/2004 | Justis et al. |
| 6,245,072 | B1 | 6/2001 | Zdeblick et al. | 6,783,528 B2 | 8/2004 | Vincent-Prestigiacomo |
| 6,248,104 | B1 | 6/2001 | Chopin et al. | 6,851,430 B2 | 2/2005 | Tsou |
| 6,248,106 | B1 | 6/2001 | Ferree | 6,916,319 B2 | 7/2005 | Munting |
| 6,258,097 | B1 | 7/2001 | Cook | 6,916,330 B2 | 7/2005 | Simonson |
| 6,261,287 | B1 | 7/2001 | Metz-Stavenhagen | 6,929,606 B2 | 8/2005 | Ritland |
| 6,264,658 | B1 | 7/2001 | Lee et al. | 6,951,538 B2 | 10/2005 | Ritland |
| 6,267,763 | B1 | 7/2001 | Castro | 6,955,678 B2 | 10/2005 | Gabriel et al. |
| 6,267,764 | B1 | 7/2001 | Elberg | 6,966,910 B2 | 11/2005 | Ritland |
| 6,267,765 | B1 | 7/2001 | Taylor et al. | 6,974,480 B2 | 12/2005 | Messerli et al. |
| 6,270,498 | B1 | 8/2001 | Michelson | 6,991,632 B2 | 1/2006 | Ritland |
| 6,273,914 | B1 | 8/2001 | Papas | 7,008,431 B2 | 3/2006 | Simonson |
| 6,283,966 | B1 | 9/2001 | Houfburg | 7,166,073 B2 | 1/2007 | Ritland |
| 6,287,309 | B1 | 9/2001 | Baccelli et al. | 7,207,992 B2 | 4/2007 | Ritland |
| 6,287,313 | B1 | 9/2001 | Sasso | 7,214,186 B2 | 5/2007 | Ritland |
| 6,287,343 | B1 | 9/2001 | Kuslich et al. | 2001/0005796 A1 | 6/2001 | Zdeblick et al. |
| 6,290,700 | B1 | 9/2001 | Schmotzer | 2001/0010021 A1 | 7/2001 | Boyd et al. |
| 6,293,949 | B1 | 9/2001 | Justis et al. | 2001/0012942 A1 | 8/2001 | Estes |
| 6,296,609 | B1 | 10/2001 | Brau | 2001/0027320 A1 | 10/2001 | Sasso |
| 6,299,614 | B1 | 10/2001 | Kretschmer et al. | 2001/0047207 A1 | 11/2001 | Michelson |
| 6,302,842 | B1 | 10/2001 | Auerbach et al. | 2002/0011135 A1 | 1/2002 | Hall |
| 6,309,390 | B1 | 10/2001 | Le Couedic et al. | 2002/0016592 A1 | 2/2002 | Branch |
| 6,309,391 | B1 | 10/2001 | Crandall et al. | 2002/0022764 A1 | 2/2002 | Smith |
| 6,312,432 | B1 | 11/2001 | Leppelmeier | 2002/0029082 A1 | 3/2002 | Muhanna |
| 6,332,883 | B1 | 12/2001 | Zucherman et al. | 2002/0045904 A1 | 4/2002 | Fuss et al. |
| 6,342,056 | B1 | 1/2002 | Mac-Thoing et al. | 2002/0049368 A1 | 4/2002 | Ritland |
| 6,342,057 | B1 | 1/2002 | Brace | 2002/0058948 A1 | 5/2002 | Arlettaz |
| 6,348,058 | B1 | 2/2002 | Melkent et al. | 2002/0068973 A1 | 6/2002 | Jackson |
| 6,354,176 | B1 | 3/2002 | Nordlin | 2002/0068975 A1 | 6/2002 | Teitelbaum et al. |
| 6,355,038 | B1 | 3/2002 | Pisharodi | 2002/0077632 A1 | 6/2002 | Tsou |
| 6,361,541 | B1 * | 3/2002 | Barnhart ............ 606/108 | 2002/0082695 A1 | 6/2002 | Neumann |
| 6,368,350 | B1 | 4/2002 | Erickson et al. | 2002/0107571 A1 | 8/2002 | Foley |
| 6,368,351 | B1 | 4/2002 | Glenn et al. | 2002/0107572 A1 | 8/2002 | Foley et al. |

| | | |
|---|---|---|
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0220689 A1 | 11/2003 | Ritland |
| 2003/0225364 A1 | 12/2003 | Kraft et al. |
| 2003/0236447 A1 | 12/2003 | Ritland |
| 2004/0002708 A1 | 1/2004 | Ritland |
| 2004/0073229 A1 | 4/2004 | Yang |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0143737 A1 | 6/2005 | Paffard et al. |
| 2005/0149023 A1 | 7/2005 | Ritland |
| 2005/0149191 A1 | 7/2005 | Cragg et al. |
| 2005/0192575 A1 | 9/2005 | Pacheco |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2007/0016193 A1 | 1/2007 | Ritland |
| 2008/0132904 A1 | 6/2008 | Usher et al. |

FOREIGN PATENT DOCUMENTS

| | | |
|---|---|---|
| FR | 2796828 | 2/2001 |
| WO | WO 99/40866 | 8/1999 |
| WO | WO 00/18306 | 4/2000 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 2004/075778 | 9/2004 |
| WO | WO 2004/089244 | 10/2004 |

OTHER PUBLICATIONS

International Preliminary Report on Patentability for International (PCT) Application No. PCT/US04/16446, mailed Dec. 8, 2005.
Office Action dated Aug. 7, 2009, issued in U.S. Appl. No. 11/774,806.
Office Action dated Oct. 30, 2007, issued in U.S. Appl. No. 11/228,106.
Final Office Action dated Jul. 9, 2008, issued in U.S. Appl. No. 11/228,106.
Notice of Allowance dated Oct. 1, 2008, issued in U.S. Appl. No. 11/228,106.
Examiner Interview Summary dated Dec. 11, 2009, issued in U.S. Appl. No. 11/774,806.
Final Office Action dated Mar. 22, 2010, issued in U.S. Appl. No. 11/774,806.
International Search Report for PCT/US04/16446, Oct. 18, 2005.
U.S. Appl. No. 10/788,172, filed Feb. 25, 2004, Ritland.
U.S. Appl. No. 10/776,094, filed Feb. 10, 2004, Ritland.
U.S. Appl. No. 10/745,068, filed Dec. 22, 2003, Ritland.
U.S. Appl. No. 10/624,234, filed Jul. 21, 2003, Ritland.
Web pages, http://www.brainlab.com, Apr. 2, 2002.
U.S. Appl. No. 11/091,970, filed Mar. 28, 2005, Ritland.
U.S. Appl. No. 11/069,390, filed Mar. 1, 2005, Ritland.
Caspar; "Technique of Microsurgery: Microsurgery of the Lumbar Spine: Principles and Techniques in Spine Surgery"; *Aspen Publications*; 1990; 105-122.
Hilton et al.; "Meditronic Sofamor Danek METRX Microdiscectomy Surgical Technique Brochure"; 2000.
Kambin; "Arthroscopic Microdiscectomy: Minimal Intervention in Spinal Surgery"; *National Library of Medicine*; 1991; 67-100.
Kambin; "Percutaneous Posterolateral Discectomy"; *Clincial Orthopaedics and Related Research, Section II*; 145-154119.
Savitz; "Same-Day Microsurgical Arthroscopic Latera-Approach Laser-Assisted (SMALL) Fluoroscopic Discectomy"; *Journal of Neurosurgery*; Jun. 1994; 1039-1045.
Schaffer et al.; "Percutaneous Posterolateral Lumbar Discectomy and Decompression with a 6.9 Millimeter Cannula"; *Journal of Bone and Joint Surgery*; 1991; 822-831.
Sofamor Danek Video Systems Brochure.
Wiltse; "New Uses and Refinements of the Paraspinal Approach to the Lumbar Spine"; *Spine*; 1988; 13(6):696-706.
U.S. Appl. No. 10/165,991, Simonson.
U.S. Appl. No. 11/425,987, Ritland.
China Chemical Reporter, "Rapid Development of Polyether Ether Ketone", CNCIC Chemdata Inc., 2004, 2 pages.
Green, "Body Building—Medical Materials for Systems and Scaffolding," Materials World, Journal of the Institute of Materials, vol. 10, No. 2, 2001, 4 pages.
Green, "Effects of Gamma Sterilisation on Implant Grade Polyetheretherketone," Invibio Inc., Lancashire, United Kingdom, undated, 1 page.
Green, "In Vivo Biostability Study on Polyaryletheretherketone Biomaterial," Invibio Inc., Lancashire, United Kingdom, undated, 2 pages.
Green, et al., "A Polyaryletherketone Biomaterial for Use in Medical Implant Applications," Lancashire, United Kingdom, 2001, 1 page.
Green, et al., "Polyetheretherketone Polymer and Compounds for Surgical Applications," Lancashire, United Kingdom, undated, 9 pages.
Green, Stuart, "PEEK-Optima Polymer in the Implantable Medical Device Industry," Invibio Inc., Lancashire, United Kingdom, undated, 2 pages.
Invibio, Biomaterials Solutions, "High Performance PEEK-Optima Biocompatible Polymer Chosen for Dental Abutment Healing Caps," Invibio Inc., Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.
Invibio, Biomaterials Solutions, "PEEK-Classix," Invibio Inc., Lancashire, United Kingdom, 2003, 2 pages.
Invibio, Biomaterials Solutions, "PEEK-Optima Polymer: Performance Purity Flexibility Endurance," Invibio inc., Lancashire, United Kingdom, 2004, 3 pages.
Invibio, Biomaterials Solutions, "PEEK-Optima, Composite Hip," Invibio Inc., Lancashire, United Kingdom, undated, 2 pages.
Invibio, Biomaterials Solutions, "PEEK-Optima, Spiked Washers," Invibio Inc., Lancashire, United Kingdom, undated, 1 page.
Tangram Technology Ltd., "Polymer Data File: Polyether Ether Keotone-PEEK," Available at http://www.tangram.co.uk/TI-Polymer-PEEK.html, 2001, 5 pages.
"New Minimally Invasive Techniques, Improve Outcome of Spine Surgeries", Medtronic Sofamor Danek.

* cited by examiner

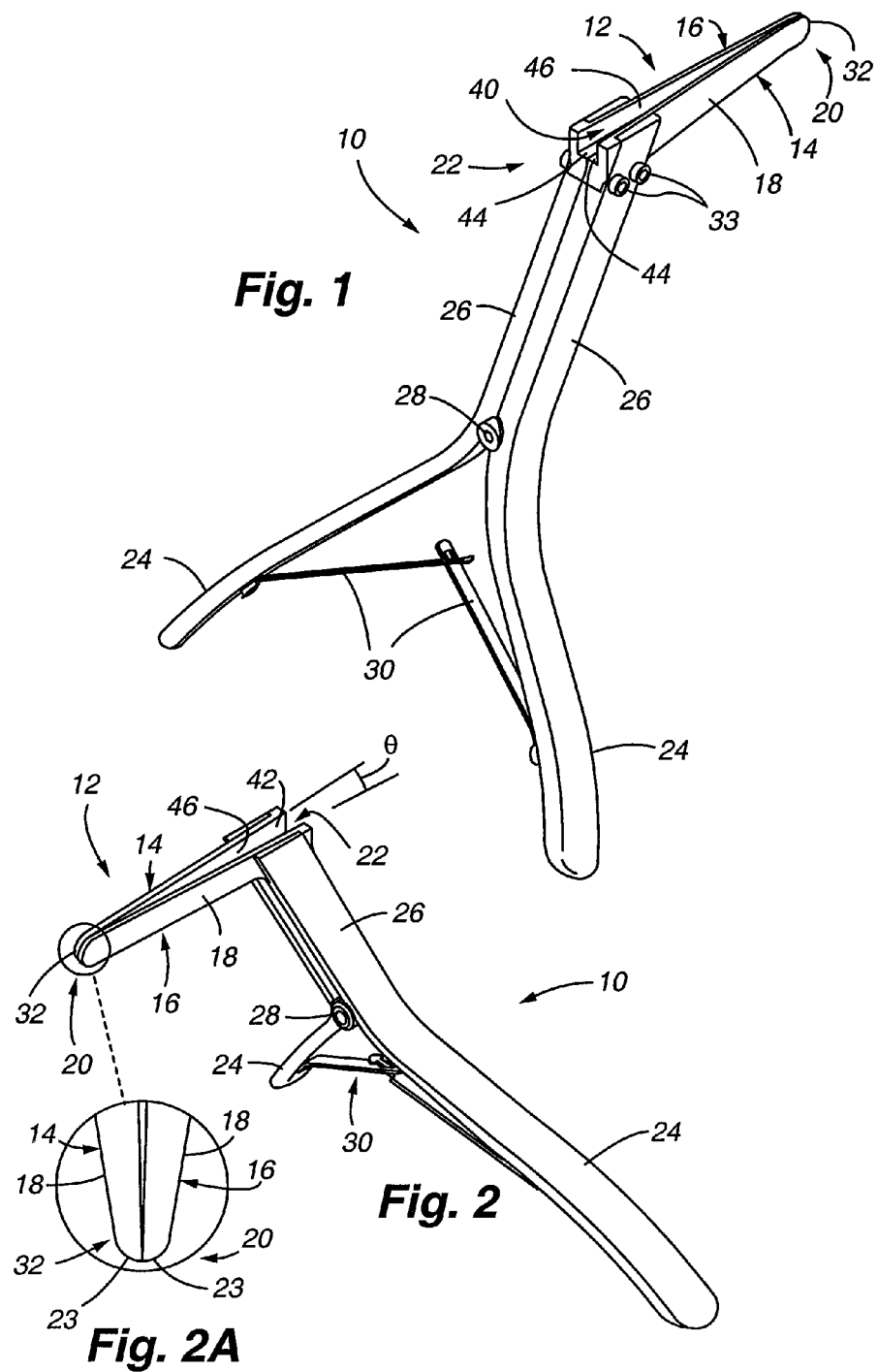

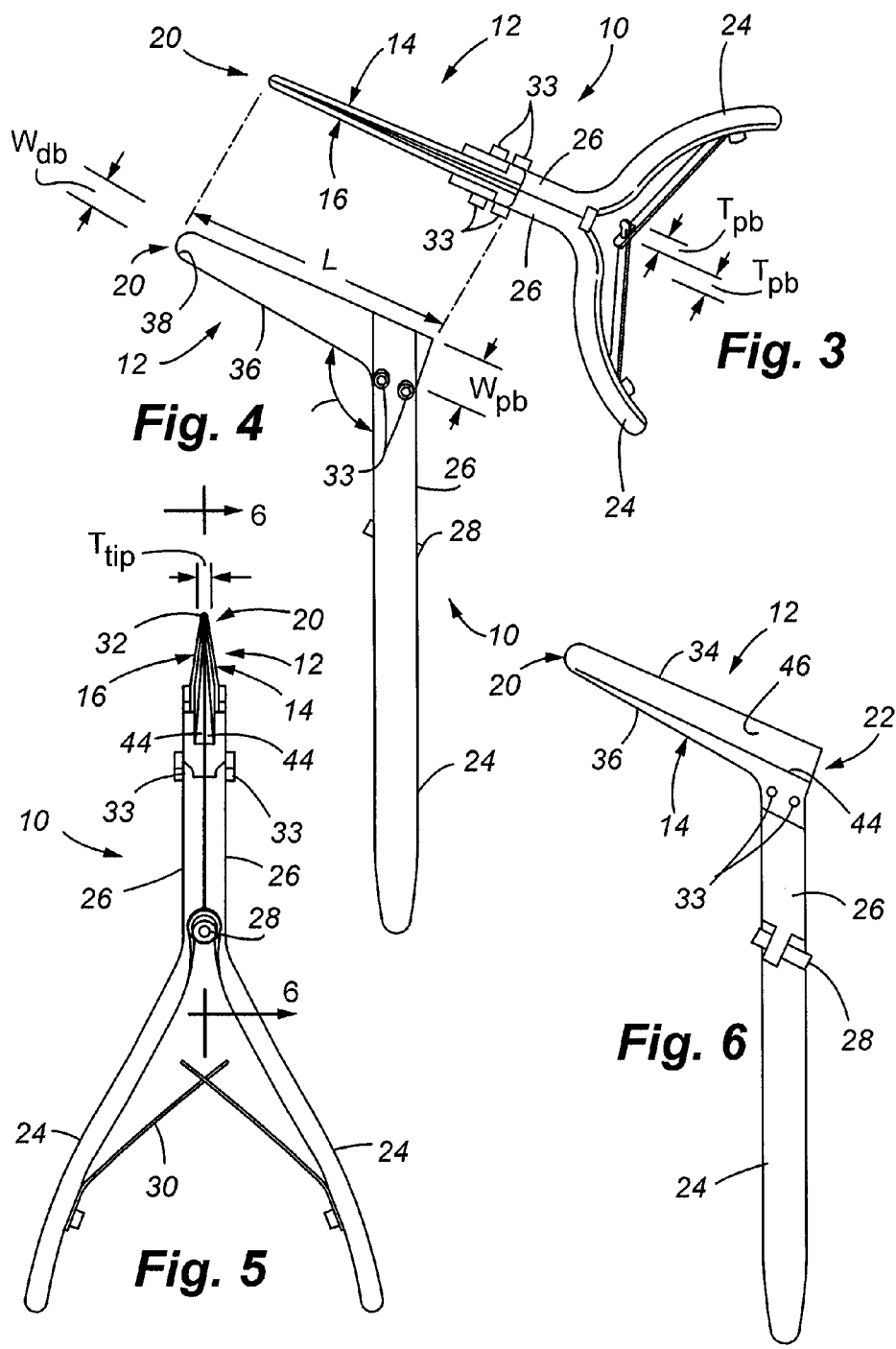

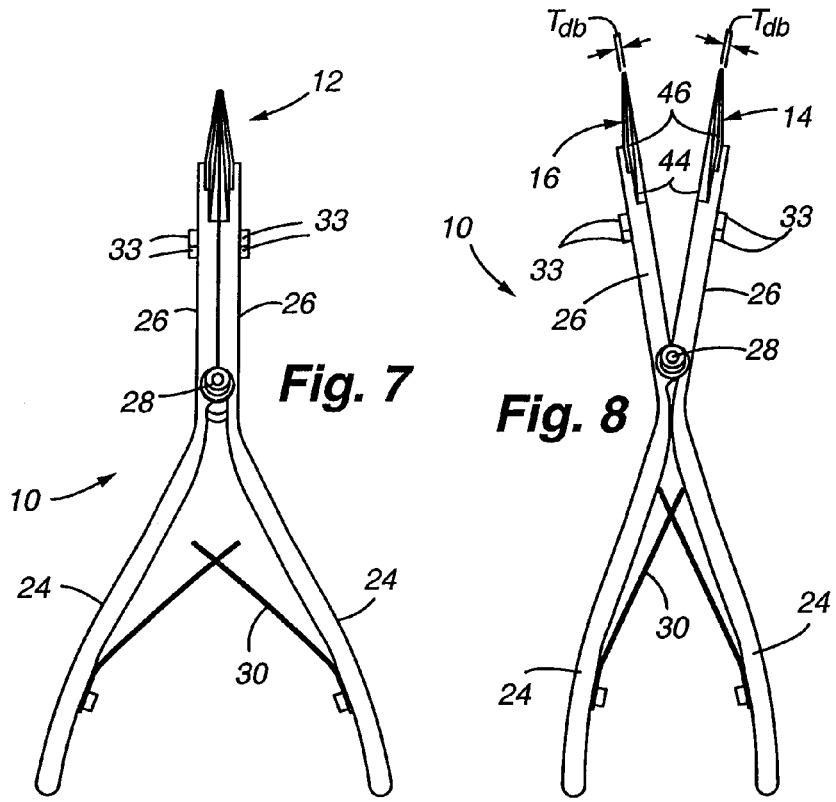
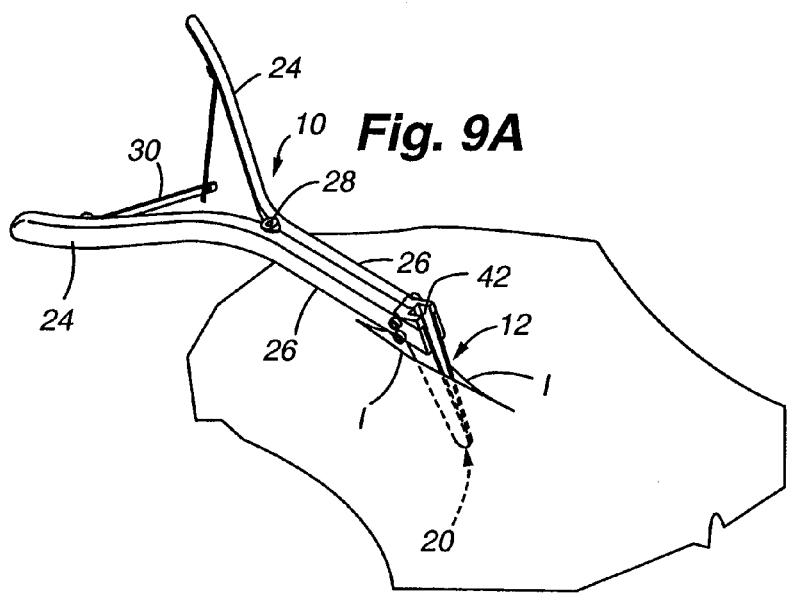

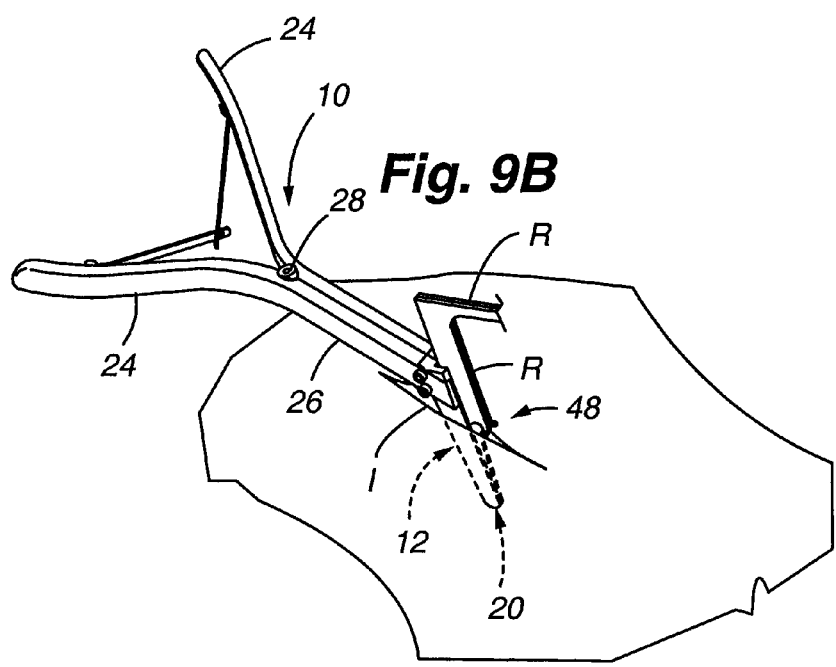

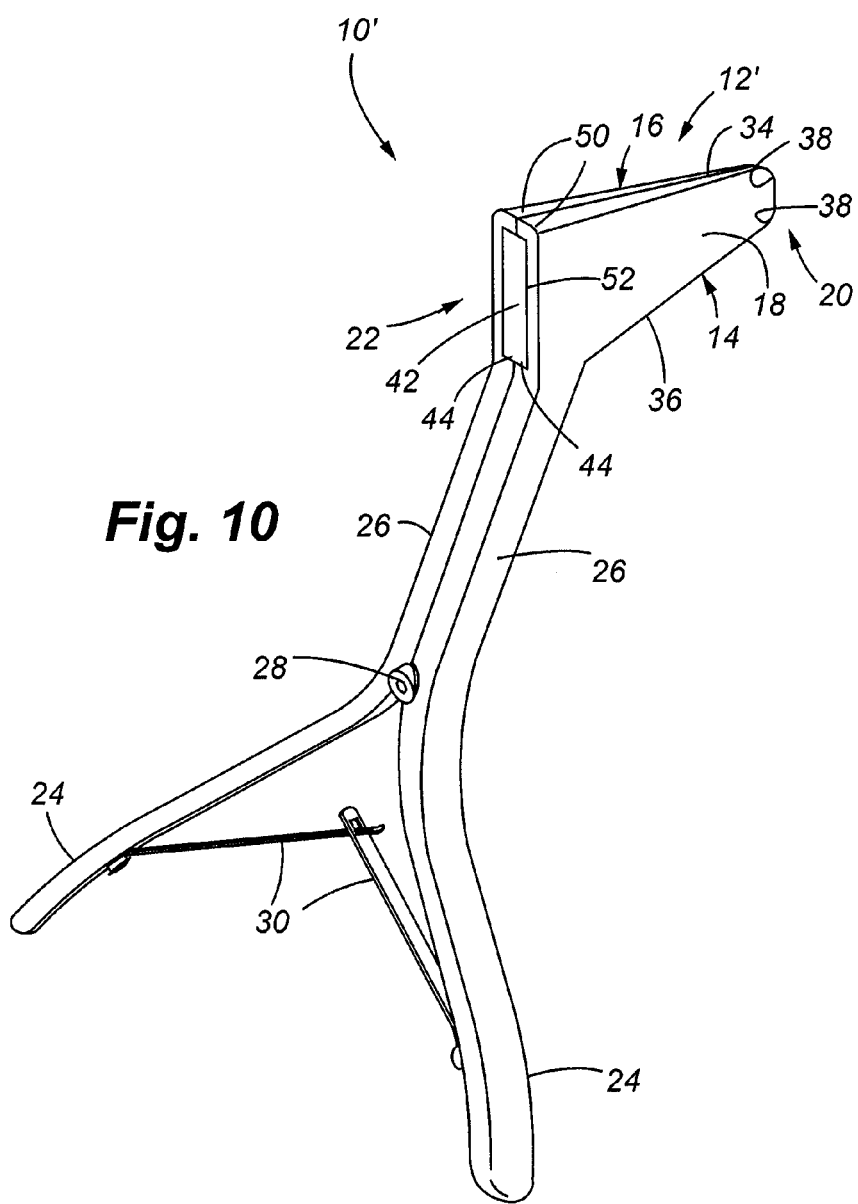

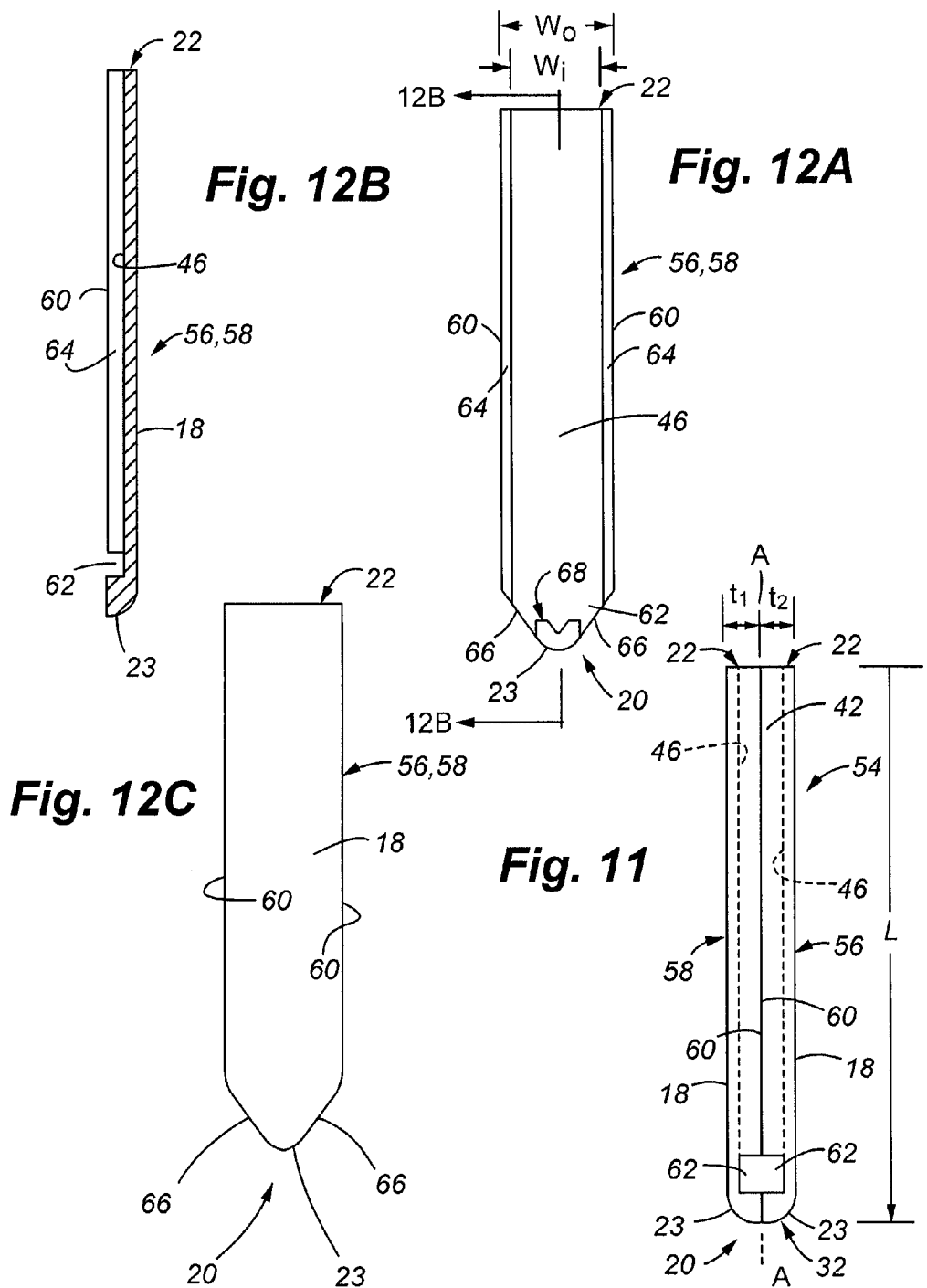

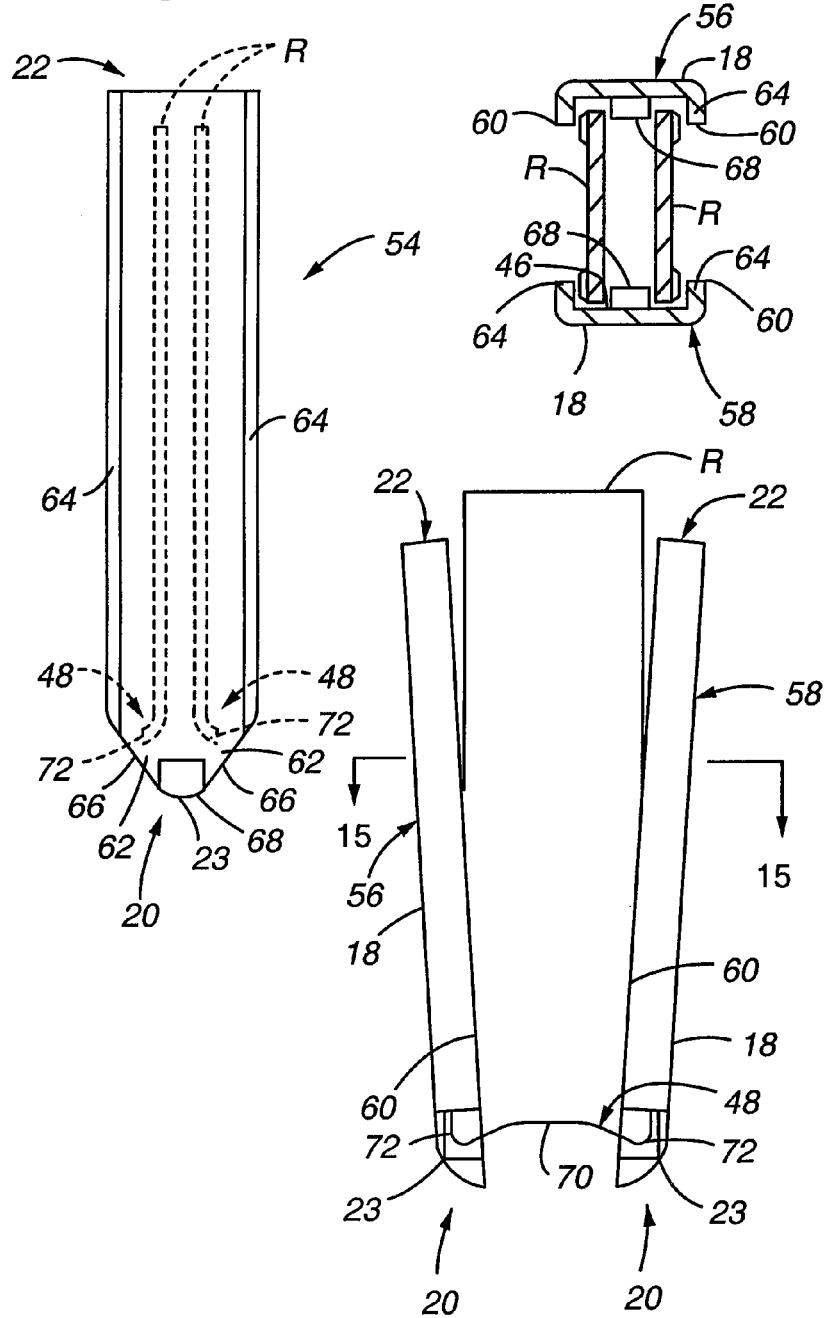

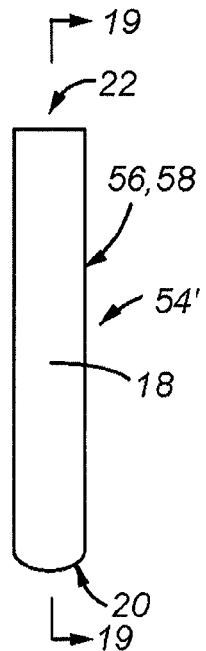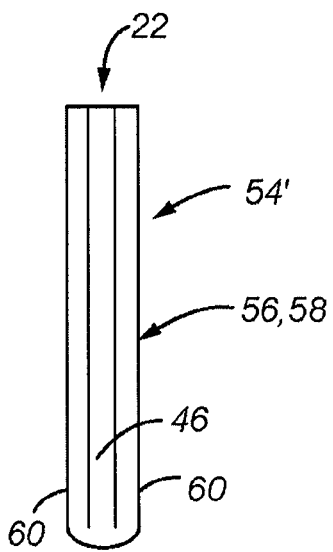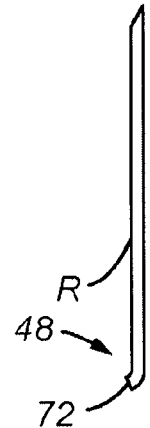
Fig. 16    Fig. 17    Fig. 18A
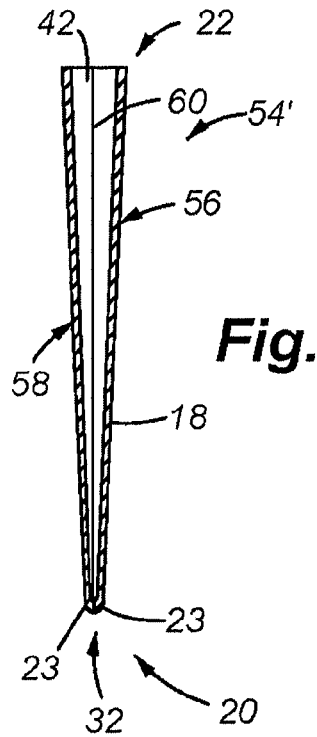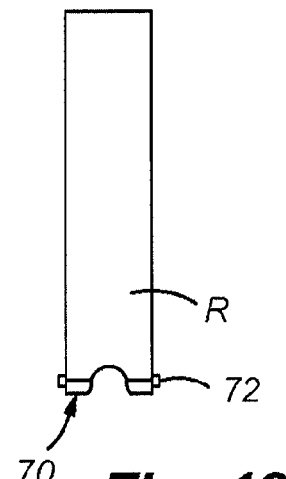
Fig. 19    Fig. 18

INTERMUSCULAR GUIDE FOR RETRACTOR INSERTION AND METHOD OF USE

CROSS-REFERENCE TO RELATED APPLICATIONS

Priority is claimed from U.S. Provisional Patent Application No. 60/472,978 filed May 22, 2003 entitled "INTERMUSCULAR GUIDE FOR RETRACTOR INSERTION AND METHOD OF USE," which is incorporated by reference in its entirety.

FIELD OF THE INVENTION

The present invention relates to devices used in surgical procedures, and more particularly, to a device initially inserted in an incision and subsequently used to guide a retractor or other tool or device into place.

BACKGROUND OF THE INVENTION

Surgical retraction using a pair of blades to maintain exposure for the surgical site is a long established practice. The blades may be fixed to a retractor mechanism or interchangeable on a retractor body.

Establishing a retractor in small space is a problem that has been addressed in a variety of ways. The original Weitlaner retractor uses interlocking teeth on the retractor to provide a smooth retractor for insertion with teeth on the distal portion to engage the underside of the muscle or tissue planes. The teeth are interlocked when the retractor is in a closed position and exposed as soon as the retractor starts to open. Many other retractors with a similar hooked or curved surface at the tip of the blade require temporary retraction to establish the blades in position. Some retractors using interchangeable blades allow temporary retraction of tissue and individual placement of blades before attaching to a retractor body.

Presently, placing such a retractor is difficult and requires a larger opening with use of temporary retractors to hold open the plane. Additionally, it is frequently difficult to get the retractor all the way down to the bony surface without catching some fascicles of muscle tissue in the process. When using a retractor tip with a central portion removed to allow placement over the prominence of the lamina, it is frequently difficult to not get one side out of plane and disrupt muscle fibers during placement.

The presently available retractors can be difficult to initially insert into a surgical site, because they are designed for maintaining an opening for the surgeon to perform his or her work, but they are not designed for neatly creating the initial opening. Thus, there exists a need for a device that can be used to establish a path for placement of a retractor in a tight intermuscular or transmuscular plane with minimal dissection or exposure required.

SUMMARY OF THE INVENTION

In summary, the present invention is a guide that is inserted through an incision and into tissue and is used as a pathway for inserting a retractor or other device into a deeper portion of tissue.

The present invention provides a means to establish a path for placement of a retractor in a tight intermuscular or transmuscular plane with minimal dissection or exposure required.

The specific application envisioned is for lumbar exposure, but it is more generally useful for exposure in situations requiring placement of a tool, such as a bladed retractor where tissue are likely to interfere with retractor placement. Its function is analogous to that of a shoehorn for helping to get into a tight shoe.

In the situation of an intermuscular placement, a plane may be opened with a dissector parallel with the muscle fascicles. It is generally simple in the lumbar spine to open a plane directly to the laminar and articular surface through the muscle. However, it is frequently difficult to place a retractor with any kind of lip to retain the deep margin of the muscle if a limited approach is made. The present invention provides an opening and access through this plane to the bony surface. It provides protection for the retractor blade and a path to the bone for a retractor blade or blades with or without a deep lip, teeth or other surface feature to retain the deep tissue out of the surgical field.

In one embodiment of the present invention, the guide includes is a pair of blade members interconnected to handles. The blade members include at least one tapered shoulder that narrows in thickness along its length, such that the blade portion formed by the paired blade members is essentially a wedge-shaped structure when in the closed position. After insertion of the guide into an incision, a retractor may be passed though a slot within the blade portion of the guide.

Another embodiment of the present invention is a guide for a retractor comprising a first member and a second member, each of the first and second members having a pair of spaced apart side flanges and a recessed interior surface between the side flanges, wherein a slot is formed upon pairing an inside edge of the first member with an inside edge of the second member. The slot is adapted for receiving the retractor therein.

In yet another embodiment of the present invention, a guide for a retractor comprises a first member and a second member. At least one of the members includes at least one tapered shoulder that narrows in thickness along its length, such that the paired members essentially form a wedge-shaped structure when in the closed position. A longitudinal slot through the paired members is adapted for receiving the retractor therein.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1 is a perspective view of an embodiment of the present invention;

FIG. 2 is an alternate perspective view of the device shown in FIG. 1;

FIG. 2A is a detail elevation view of the tip of the blade portion shown in FIG. 2;

FIG. 3 is a front perspective view of the device shown in FIG. 1;

FIG. 4 is a side elevation view of the device shown in FIG. 3;

FIG. 5 is a top elevation view of the device shown in FIG. 1;

FIG. 6 is a side elevation view of the inside of one blade member of the device shown in FIG. 1;

FIG. 7 is bottom elevation view of the device shown in FIG. 1;

FIG. 8 is a top elevation view of the device shown in FIG. 1 in an open position;

FIG. 9A is a perspective view of the device shown in FIG. 1 after being inserted into an incision;

FIG. 9B is a perspective view of the device shown in FIG. 9A after a retractor is inserted into the slot of the blade portion and partially lowered through the incision;

FIG. 10 is a perspective view of an alternate embodiment of the present invention;

FIG. 11 is a front elevation view of a separate embodiment of the present invention;

FIG. 12A is an interior side elevation view of one member of the device shown in FIG. 11;

FIG. 12B is cross-sectional view of the device shown in FIG. 12A taken along line 12B-12B as shown in FIG. 12A;

FIG. 12C is a side elevation view of the exterior of the device shown in FIG. 11;

FIG. 13 is an interior side elevation view of the guide shown in FIG. 11 with a retractor used in combination with the guide, where the retractor is shown in phantom;

FIG. 14 is a front elevation view of the guide shown in FIG. 11 with a retractor advanced within the guide;

FIG. 15 is a cross-sectional view of the guide and retractor of FIG. 11 taken along line 15-15 of FIG. 14;

FIG. 16 is side view of the exterior of a modification of the guide shown in FIG. 12C;

FIG. 17 is a side elevation view of the interior of the device shown in FIG. 16;

FIG. 18 is a front elevation view of a retractor that can be used with the guide shown in FIGS. 16 and 17;

FIG. 18A is front elevation view of the retractor shown in FIG. 18;

FIG. 19 is a cross sectional view of the guide shown in FIGS. 16 and 17 with paired members and taken along line 19-19 as shown in FIG. 16;

DETAILED DESCRIPTION OF THE INVENTION

Figure 20:
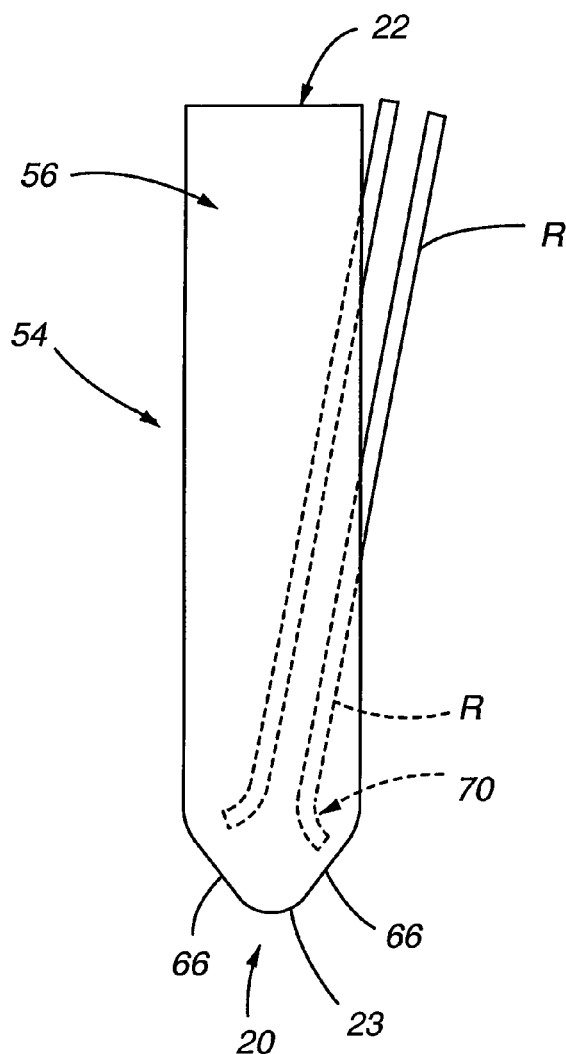
FIG. 20 is an elevation view of the guide shown in FIG. 12C used with a retractor having an offset entry orientation.

The guides of the present invention are intended to function generally with a retractor using one or more blades, for example, paired blades, where the retractor typically has some sort of curved surface or teeth at its distal portion. The teeth of the retractor are typically used to engage the undersurface of muscle or tissue to maintain retraction of those structures, and to minimize the risk of displacement of the retractor, and/or minimize the risk of displacement of the muscle or tissue from escaping retraction and falling back into the field of view.

Referring to FIGS. 1-9B, a retractor guide constructed in accordance with an embodiment of the present invention is generally identified by the reference numeral 10. As best seen in FIGS. 1 and 2, the retractor guide 10 includes a blade portion 12 comprising a first blade member 14 and a second blade member 16. First blade member 14 and second blade member 16 are generally apposed and are structures that are mirror images of each other. The blade portion 12 of guide 10 preferably approximates a wedge-type of shape.

The first blade member 14 and second blade member 16 include a generally smooth exterior surface 18 that extends from a distal end 20 to a proximal end 22 of the blade portion 12. The distal end 20 of each blade member 14 and 16 preferably includes a substantially quarter-rounded tip 23. The smooth exterior surface 18 and substantially quarter-rounded tips 23 of each blade member 14 and 16 provide a surface for sliding the blade portion 12 against tissue, preferably without cutting, catching or tearing of the tissue. Thus, the smooth exterior surface 18 preferably includes rounded edges, such as the quarter-rounded tips 23. The smooth exterior surface 18 allows the relatively small and narrow distal end 20 of the first and second blade members 14 and 16 to be inserted through tissue without causing unnecessary amounts of damage to the tissue overlying and/or surrounding the interior surgical site.

The blade portion 12 is preferably interconnected to handles 24 by elongated extension portions 26 that are joined at a pivot point 28 such as a hinge or pin. The handles 24 are used to open the blade portion 12 and separate the first blade member 14 and the second blade member 16. The handles 24 preferably include a spring mechanism 30 to maintain a closed position. The spring mechanism 30 provides a means for biasing the handles in a closed position. Thus, the spring mechanism 30 could comprise one or more of a variety of biasing structures, such as a spring or resilient rubber or plastic. When not squeezing the handles 24 together, the first blade member 14 is preferably positioned adjacent and substantially in contact with the second blade member 16.

As noted, the blade portion 12 is generally wedge-shaped, which facilitates placement of the distal end 20 of the blade portion through muscle and/or other tissue, with the proximal end 22 having a larger dimension than distal ends 20, where the larger proximal end 22 is configured for receiving a further device such as a retractor, as will be discussed below. The structure of the blade portion 12 allows the first blade member 14 and second blade member 16 to be quickly, smoothly and easily inserted through tissue. When closed, the first blade member 14 is situated adjacent the second blade member 16. As best shown in FIG. 2, the distal ends 20 of the first blade member 14 and second blade member 16 are designed to form a tip 32 of blade portion 12 that is relatively smooth and can be easily inserted into tissue, such as along a plane formed between muscle fibers.

The dimensions of the present invention, its various embodiments, and its components may vary. Dimensions can be modified and adapted for uses other than those involving lumbar or spinal surgery. For example, modifications and adaptations may be made to the guide for using the guide during animal surgeries. Any such modifications are encompassed within the scope of the invention. For example, a larger and/or modified guide may be used for equine spinal surgery. For purposes of providing examples for the present application, the guide is explained for use in human spinal surgery of the lumbar spine; however, it is to be understood that the guide may be used for other types of surgeries.

Referring now to FIG. 8, in one preferred embodiment, the distal blade thickness "$T_{db}$" of the distal end 20 of each of the first blade member 14 and second blade member 16 is about 1 mm. As defined herein, the thickness is the distance across the blade from its right side to the left side. The tip 32 of the blade potion 12 is the rounded end formed by the distal end 20 of the first blade member 14 when closed against the distal end 20 of the second blade member 16. That is, the tip 32 is the distal end of the blade portion 12. The tip 32 preferably does not include an opening at the very end of the blade portion 12; thus, the distal end 20 of first blade member 14 fits sufficiently with the distal end 20 of the second blade member 16 such that tissue will typically not move into or slip between the members 14 and 16 as the closed blade portion 12 is being inserted into the patient to form a surgical opening from the incision at the skin surface down to the boney surface of the subject vertebra.

As can be seen in FIG. 5, preferably, the tip thickness "$T_{tip}$" of the tip 32 of the blade portion 12 is approximately 2 mm. This thickness provides a relatively narrow device with which to initiate separation of tissue. The blade portion 12 preferably thickens toward the proximal end 22 of each of the first blade member 14 and second blade member 16. The thicker proximal end 22 is configured for receiving a separate device, such as a single or dual bladed retractor. In one preferred embodiment, the proximal end 22 of each of the first blade member 14 and second blade member 16 has a proximal blade thickness "$T_{pb}$" of is about 4-10 mm, and more preferably about 5-8 mm, and more preferably yet, about 6 mm. Thus, the combined thickness of the proximal ends 22 of first blade member 14 and second blade member 16 that forms the blade portion 12 is about 8-20 mm, and more preferably, about 10-16 mm, and more preferably yet, about 12 mm.

Referring now to FIG. 2, as noted above, the blade portion 12 of guide 10 generally has approximately a wedge-shape. The first blade member 14 and second blade member 16 are preferably separated by a blade separation angle "θ" that is preferably between about 1-45 degrees, and more preferably between about 1-30 degrees, and more preferably yet, between about 1-10 degrees, and still more preferably yet, between about 4 to 8 degrees. The preferred relatively small angle between the first blade member 14 and second blade member 16 allows the guide to be inserted into the tissue of the patient without creating unnecessary amounts of tissue displacement to reach the posterior portions of the vertebra and allow insertion of a retractor through the guide 10.

As can be seen in the side view of the guide 10 shown in FIG. 4, the blade portion 12 is preferably angled relative to the handles 24. More particularly, the blade portion 12 is offset from the extension portion 26 of the handles 24 by a handle separation angle "φ" of between about 45 and 135 degrees, and more preferably yet, an angle of about 120 degrees separates the blade portion 12 and the extensions 26 of the handles 24. This angle is suited for lumbar surgery where the handle separation angle φ is substantially similar to the angle need for pedicle screw insertion.

Referring still to FIG. 4, for surgeries involving access to the lumber vertebrae, the length of the blade allows for access from the incision at the skin surface to the interior surgical site, such as the posterior portion of a vertebra. The blade length "L", therefore, is defined herein as the distance between the distal end 20 of the blade members 14, 16 and the proximal end 22 of the blade members 14, 16. The blade portion 12 is preferably between about 25 to 150 mm long, and more preferably between about 50 to 125 mm long, and more preferably yet, about 75 mm long. This value allows the blades to extend from the deeper posterior portion of the vertebra to the skin surface. Blades that are too short will not reach the desired interior surgical site, and blades that are excessively long will be clumsy and not easily maneuvered. Thus, a properly sized blade portion 12 is desirable, and is partially dependent upon the size and dimensions of the subject patient. Accordingly, interchangeable blades can be provided for use. Alternatively, a surgeon may have a plurality or set of guides having different dimensions. As shown in FIG. 1, the blade members 14 and 16 are interconnected to the extension portions 26 using means for connecting, such as one or more screws or bolts 33. Alternatively, the blade portion 12 may be formed integrally with the extension portions 26 and handles 24, as shown in FIG. 10.

Referring still to FIG. 4, an exterior side elevation view guide 10 is shown. First and second blade members 14, 16 have a tapered width, where the width of the blades is herein defined as the distance from a front 34 of the blade members 14, 16 to a rear 36 of the blade members 14, 16. A distal blade width "$W_{db}$" of the blade members 14, 16 at the distal end 20 is preferably about 3-15 mm, and more preferably, about 5-10 mm, and more preferably yet, about 8 mm. The distal end 20 of each member 14, 16 includes rounded corners 38 to provided a smooth insertion of the member 14, 16 into tissue. A proximal blade width "$W_{pb}$" of the blade members 14, 16 at the proximal end 22 is preferably about 8-20 mm, and more preferably about 10-15 mm, and more preferably yet, about 13 mm. Thus, the width of the blade members 14, 16 preferably tapers along their length L, wherein the width increases from the distal end 20 to the proximal end 22. Providing a greater blade width at the proximal end allows the surgeon more mobility and access in terms of turning tools to obtain a desirable angle at the top of the subject vertebra. The dimensions noted above provide for sufficient access, without creating too small a guide or too large a guide for a typical incision that is necessary to span a single vertebral disc. In addition, the dimensions and allow access for using a retractor with the guide 10 in order to contact the vertebrae that are adjacent the subject vertebral disc.

Referring now to FIGS. 1 and 6, the blade portion 12 preferably includes an interior region 40 that is suited for receiving a separate device, such as a retractor. More particularly, the interior region 40 preferably includes a slot 42 that extends from the proximal end 22 to a location near the distal end 20 of the blade portion 12. The slot 42 is formed by inside surface structure of the first blade member 14 when situated adjacent the second blade member 16. At least one of the first blade member 14 and second blade member 16 preferably include a tapering shoulder 44 along an inner surface 46. In one preferred embodiment, the shoulder 44 is preferably set about 9 mm rearward or back from the front 34 at the proximal end 22 of each member 14, 16. In addition, the when the blade portion 12 is closed, the slot 42 is about 4 to 6 mm across, and more preferably, about 5 mm across. Thus, in plan view the slot 42 in the blade portion 12 is about 9 mm wide by about 5 mm across. The slot 42 is sized for receiving a separate tool, such as a retractor R. As discussed below, the distal end of the retractor R can be received in the slot 42 of the guide 10 and guided to the interior surgical site.

Referring now to FIG. 6, a side view of the inside of blade member 14 is shown. The inside of blade member 16 is substantially similar to the inside of blade member 14. The shoulder 44 is preferably thickest at the proximal end 22 of blade members 14 and 16. The shoulder 44 preferably tapers in thickness to zero or nearly zero at a location at or near the distal end 20 of blade members 14 and 16. It should be noted that the shoulder 44 can be limited to only one blade member 14 or 16. More particularly, one optional configuration is to construct a blade portion where only one blade member 14 or 16 has a tapering shoulder 44.

Referring now to FIGS. 9A and 9B, in use, the surgeon first makes an incision "I" over the interior surgical site. Through the incision I, the surgeon then inserts the distal end 20 of the closed blade portion 12 of the guide 10. Preferably, the surgeon inserts the distal end 20 of the guide 10 along a plane formed by muscle fibers. For spinal surgery, the distal end 20 of the blade portion 12 of guide 10 is inserted until a desired depth is reached, such as the bony posterior surface or the spinous process of the vertebra (not shown). While maintaining the position of the guide 10, the surgeon then places the distal end 48 of a retractor R into the proximal end 22 of the slot 42 of the blade portion 12. The retractor R is then lowered through the slot 42 of the blade portion 12, until the distal end 20 of the blade portion 12 is reached, which corresponds with the posterior surface of the subject vertebra. At this point, the guide 10 can optionally be rotated within the incision if desired by the surgeon. The guide 10 can be gradually opened using the handles 24 and/or forced open by the larger retractor R as the retractor R is lowered; however, while the retractor R is being lowered, the first and second members 14 and 16 of the blade portion 12 protect the tissue neighboring the exterior surface 18 of the blade portion 12 from moving across the pathway of the retractor R.

Once the distal end 48 of the retractor R reaches the posterior surface of the subject vertebra, the retractor R can be opened and/or rotated to provide surgical access to the interior surgical site. In addition, the guide 10 can be extracted from the patient. Thus, the guide 10 provides relatively quick access to an interior surgical site, without causing undue tissue damage either by unnecessarily cutting tissue to reach the interior site, or by forcing a retractor R through the tissue without having a pathway established for the retractor R. The guide 10 is an improvement over tubular or cylindrical dilators because the dilators typically require placement of a plurality of different size dilators to enlarge the surgical pathway sufficiently, and this process is time consuming. In addition, the cylindrical dilators displace tissue equally in all directions; however, this is not always necessary, and in some instances can unduly stress or tear tissue. The present invention is used along what is analogous to a plane of access, where the blade portion 12 has a relatively narrow thickness T as compared to its width W from the front 34 to the rear 36 of the members 14, 16.

Referring now to FIG. 10, in an alternate embodiment, a retractor guide 10' is shown, wherein the guide 10' has a closed front 34 along its wedge-shaped blade portion 12'. More particularly, the guide 10' includes a blade portion 12' having a slot 42. However, the front 34 of the blade portion 12' includes a front lateral portion 50 along blade members 14 and 16 that essentially provide a closed slot 42 along the front 34 when the blade portion 12' is in a closed position. The front lateral portions 50 may taper in thickness along the length of the blade portion 12'.

In use, guide 10' is used in a manner similar to that of guide 10. That is, a single or dual bladed retractor is slid down the slot 42 through an aperture 52 that is contiguous with the slot 42 at the proximal end 22 of the blade portion 12' until a the desired surgical depth is achieved. The guide 10' is either opened with the handles 24, or the retractor forces open the guide portion 12' while being inserted through the slot 42. After the retractor is in place, the guide is extracted from the patient.

In a modification to the above discussed embodiments, the guides 10 and 10' may be used without handles 24 and/or extensions 26. For this variation of the device, the guides would essentially include the blade portion 12 or 12', including its blade members 14 and 16. In use, the blade portion 12 or 12' of the guide would be held together during insertion into the patient's tissue, and then removed after inserting a retractor or other tool through the guide 10, 10'.

Referring to FIG. 11, a side elevation view of a separate embodiment of the present invention is shown. Guide 54 includes a first member 56 and a second member 58, where first member 56 and second member 58 are positioned adjacent one another when the guide 54 is assembled in its closed position. First member 56 and second member 58 each include side edges 60 and a smooth exterior surface 18. Preferably, a substantial portion of side edges 60 are substantially parallel to a longitudinal axis A-A of guide 54. Prior to insertion of guide 54 in a patient's incision, side edges 60 of first member 56 are aligned substantially adjacent to side edges 60 of second member 58.

Still referring to FIG. 11, first member 56 and second member 58 each have a distal end 20 and a proximal end 22. The distal end 20 of each member 56 and 58 preferably includes a substantially quarter-rounded tip 23. When first member 56 and second member 58 are positioned adjacent each other, each quarter-rounded tip 24 sits adjacent the other and creates a substantially half-rounded end portion or tip 32.

An edge portion near the distal end 20 of first member 56 and second member 58 can optionally include a lateral aperture 62. Where use, the lateral apertures 62 can be sized to accommodate a projection located at a distal end 48 of a retractor R, as will be discussed below.

First member 56 has a thickness $t_1$ and second member 58 has a thickness $t_2$. Thicknesses $t_1$ and $t_2$ may be equal, or they may be different. In addition, the thicknesses $t_1$ and $t_2$ may vary along the length of the members 56 and 58. The overall length of guide 54 from the distal end 20 to the proximal end 22 varies with the application to which the guide 54 is applied; however, for surgeries to the lumbar vertebrae of the spine, the length L is anticipated to be similar to the lengths discussed above for guide 10.

Referring now to FIG. 12A, an elevation view of the inside of either first member 56 or second member 58 is shown. The inside of members 56 and 58 includes an inner surface 46. Bordering inner surface 46 on the sides are side edges 60. In one possible configuration, side edges 60 are raised relative to inner surface 46. More particularly, side edges 60 can be situated adjacent side flanges 64, where inner surface 46 is recessed relative to the interior side flanges 64 and side edges 60. The distal end 20 can include tapered edges 66 that lead to half-rounded tip 32. Alternatively, the distal end 20 can have more of a rectangular type of shape.

Each of the first member 56 and the second member 58 have an interior width "$W_i$," that is the width of the inner surface 46. The inside width $W_i$ is preferably wide enough to accommodate a retractor that is to be inserted into guide 54. Each of the first member 56 and the second member 58 have an outside width "$W_o$". For most posterior surgeries in the lumbar area of the spine involving only one spinal disc, guide 54 is anticipated to have an outside width $W_o$ of between about 12 and 20 millimeters.

Distal end 20 of members 56 and 58 may also optionally include an interior tip flange 68. Similar to interior side flanges 64, interior tip flange 68 is preferably raised relative to inner surface 46. Interior side flanges 64 and interior tip flange 68 on first member 56 substantially align with interior side flanges 64 and interior tip flange 68 on second member 58 such that when a surgeon places first member 56 adjacent second member 58, the two members 56 and 58 can be inserted into an incision and the flanges serve to prevent tissue from entering the guide. Furthermore, the tapered edges 66 that lead to the tip 32 also serve to form a substantially smooth surface on the edge of the guide 54 so that when a surgeon places first member 56 adjacent second member 58, the two members 56 and 58 can be inserted into tissue and used for intermuscular placement to create a plane opened by guide 54.

Referring still to FIGS. 11 and 12A, and as noted above, guide 54 can optionally include lateral apertures 62 in the vicinity of tapered edges 66 at the distal end 20 of both the first member 56 and second member 58. Apertures 62 are essentially gaps between interior side flanges 64 and interior tip flange 68. When first member 56 is paired with second member 58, lateral apertures 62 create a window for retractor blades to exit the distal end 20 of members 56 and 58 upon insertion of a retractor into the guide 54 after guide 54 is inserted to the patient's incision.

Referring now to FIG. 12B, a cross-sectional view taken along line 12B-12B of FIG. 12A shows the center profile of either first member 56 or second member 58 of a guide 54. The inner surface 46 can be seen to be recessed relative to side edge 60.

Referring now to FIG. 12C, a side elevation view of the exterior of members 56 and 58 is shown. The exterior portion of first member 56 and second member 58 is preferably a relatively smooth uninterrupted exterior surface 18.

In use, a surgeon creates an incision and then inserts guide 54 into the incision to create a pathway to an interior area of the patient. After inserting the guide 54 into the desired location, the surgeon can then insert a retractor into the guide to gain greater access to the interior surgical site of the patient. Thereafter, the guide 54 can be removed. The structure of the guide 54 therefore, serves to provide a device that is easily inserted into an incision and manipulated to the interior surgical site, while then subsequently allowing a properly configured retractor to be inserted into the guide itself to open up the tissue of the patient along a preferred plane established by the guide.

Referring now to FIGS. 13-15, guide 54 is shown with retractor R inserted into guide 54 and rotated about 90 degrees. Since inner surface 46 of first member 56 and second member 58 creates a slot 42 within guide 54, the distal end 48 and/or tip of retractor R can be inserted into the slot 42 starting at the proximal end 22 of guide 54 and advanced to the distal end 20 of guide 54. During this step, the retractor R essentially wedges apart first member 56 and second member 58 creating a larger opening that increasingly accommodates the retractor R. The retractor R can optionally be turned 90 degrees once the lateral apertures 62 are engaged by the distal end 48 of the retractor R. FIGS. 13 and 14 show the retractor R having retractor tips 70 at distal end 20 of guide 54. Retractor tips 70 of the retractor R may optionally include curved ends or projections 72 that cooperate with apertures 62 of guide 54.

Referring now to FIGS. 16 and 17, guide 54' is shown where guide 54' is a modification of guide 54 and includes a distal end 20 without tapered edges 66. FIG. 16 shows a side elevation view of the exterior of either first member 56 or second member 58 of guide 54', and FIG. 17 shows a side elevation view of the interior of either first member 56 or second member 58 of guide 54'. The interior of guide 54' preferably includes grooves 74 to engage a blade of a retractor R, where the grooves 74 and retractor R cooperate by the presence of projections 72 at the tip 70 of the retractor R that align and pass along the grooves 74 as the retractor R is inserted in the guide 54'. FIGS. 18 and 18A show an example of a retractor blade that can be used with guide 54'. FIG. 19 shows a cross section of first member 56 and second member 58 of guide 54' in a closed or paired arrangement. The guide 54 and 54' may include angled or parallel exterior surfaces 18, and the inner surface 46 may also be angled or parallel. FIG. 19 depicts guide 54' having a V-shaped cross section with angled and non-parallel exterior and interior surfaces.

Figure 21:
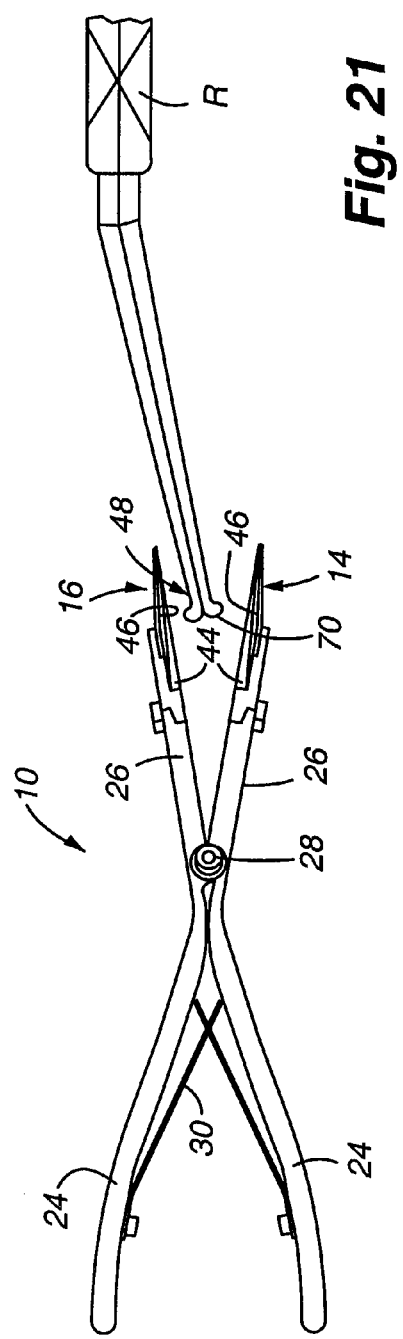
FIG. 21 is a top view of the guide shown in FIG. 1 used with a retractor having an offset entry orientation.

Referring now to FIGS. 20 and 21, in a modified method of using of using the invention, a retractor R may be inserted into a guide of the present invention by offsetting the retractor R to the side of guide. Guide 54 with an offset retractor R is shown in FIG. 20, and guide 10 with an offset retractor R is shown in FIG. 21; however, side entry could be used for any guide disclosed herein or modification thereof. Although it is anticipated that the retractor would commonly be inserted through the top of the slot 42 of the guide, the guide could optionally be partially opened, for example, such as be squeezing the handles 24 of guide 10 shown in FIG. 21, and the retractor blade(s) or a tool inserted along a side of the guide.

Figure 22A:
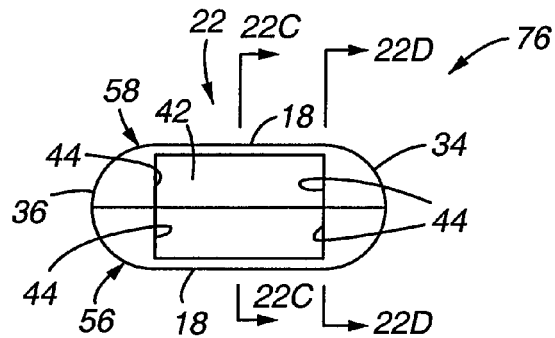
FIG. 22A is a plan view of another embodiment of the present invention.
Figures 22B, 22C, 22D:
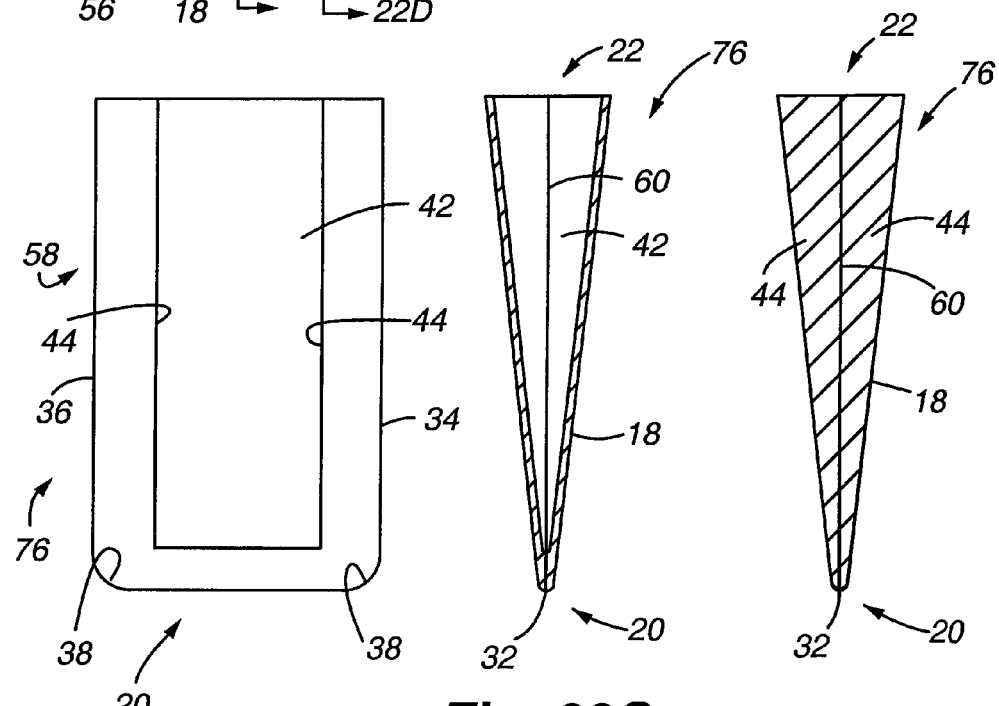
FIG. 22B is a side elevation view of the interior of a component of the guide shown in FIG. 22A.
FIG. 22C is a cross section of the device shown in FIG. 22A taken along line 22C-22C.
FIG. 22D is another cross section of the device shown in FIG. 22A taken along line 22D-22D.

Referring now to FIGS. 22A-22D, a guide 76 is shown, wherein guide 76 includes a generally oval shaped appearance in plan view and shoulders 44 that taper along their length, thereby giving the guide 76 approximately a V-shape when viewed from the front or rear. As shown in FIG. 22A, the guide includes a slot 42 for receiving a retractor or a tool. The slot narrows along the length of the guide 76. Preferably, the guide members 56 and 58 include at least one shoulder 44. The shoulder(s) 44 are preferably situated on the front an rear portions of members 56 and 58. In between the front 34 and rear 36 of the guide members 56, 58, a slot 42 is present. Although not shown, handles may be attached to the guide 76; for example, guide 76 can be substituted for the blade portion 12 shown in FIG. 1.

Figure 23A:
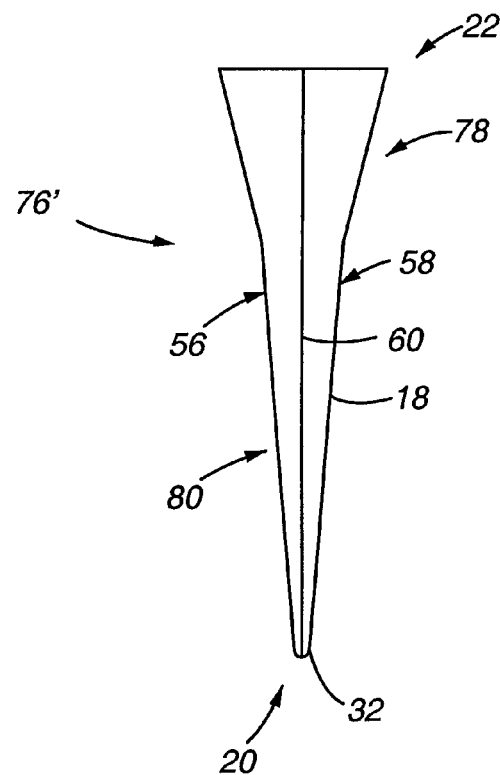
FIG. 23A is a front elevation view of a modification of the guide shown in FIGS. 22A-22D.
Figure 23B:
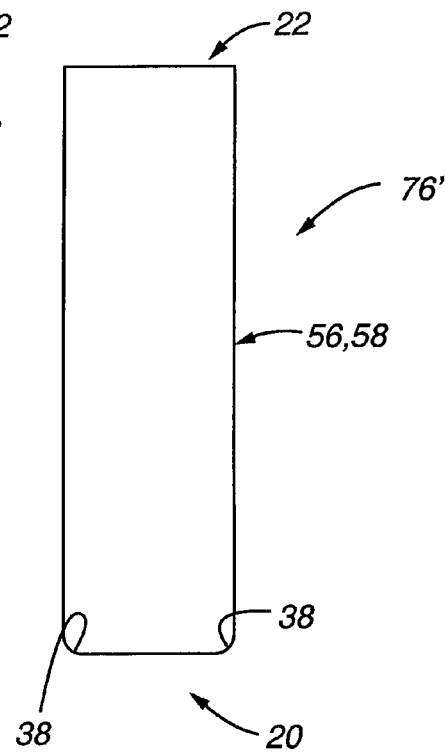
FIG. 23B is a side elevation view of the guide shown in FIG. 23A.
Figure 23C:
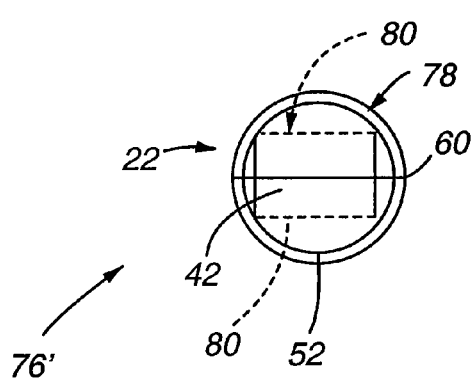
FIG. 23C is a plan view of the device shown in FIG. 23A.

Referring now to FIGS. 23A-23C, guide 76' is shown, wherein guide 76' is a modification of guide 76. Guide 76' includes non-linear edges along a V-shape when viewed from the front or back. The guide 76' features a funnel shaped top portion 78 leading to a V-shaped lower portion 80. The funnel shaped top portion 76 is preferably a truncated conical shape; however, the top portion 76 may be modified in shape, to include bulbous-type shapes, etc. The funnel shaped top portion 76 provides an expanded approach for initiating a retractor tip or the distal end of tool within the guide. The funnel shaped top portion 76 may be used with any guide disclosed herein, including modification thereof.

The dimensions of the various guides presented herein are preferably those dimensions discussed above for guide 10, including the noted modifications.

The devices disclosed herein are preferably made of materials typically used during surgical procedures. In general, tissue compatible materials are anticipated for use.

In summary, the present invention is a guide for insertion into an incision, whereby the guide acts as a pathway for inserting an additional device, such as a retractor. The nature of the blade members of the guide is that they can be used with the upper aspect separated to allow insertion of the retractor and distraction of the distal ends of the blade members being accomplished as the retractor is inserted to the depth of the surgical field. The blade members may be integrated onto a simple hinged retractor body or could be used with a retractor body accepting interchangeable blades. These different embodiments do not change the way the blade members function as guide for a retractor.

The guide is intended for insertion with its blade portion shaped to prevent any muscle intervening between the blade members. The blade members may be approximately flat with contoured tip and margins to ease insertion and avoid trauma to muscle, and/or the blade members may have a rounded outer margin so they form an ovoid or cylindrical section. The apposed blade members of the guide are preferably passed through a muscular plane to the bone. In the lumbar spine, this is accomplished to the lamina or capsule of the facet joint to a plane without muscle attachment to the bone. Once this depth is reached, the surgeon may optionally turn the retractor guide to an orientation generally perpendicular to the orientation of the muscles while maintaining contact with the deep bony or articular surface. Opening the guide with the depth maintained is then accomplished.

At this point there is a muscular plane maintained a few millimeters wide. This is not wide enough for a working space but is wide enough to allow entrance of a pair of blades on a bladed retractor to slide down to the bony surface. In many cases, the blades of the retractor may be pre-engaged to the retractor or an integral part of the retractor. Alternatively, the blades could be individually inserted in the guide before being engaged to a retractor handle. This allows use of a variety of presently available retractors with the insertion guide. Once the retractor is in position, the guide may be removed. This will then allow the retractor to be separated while maintaining position against the bony surface. Thus, the guide allows placement of a bladed retractor through a minimal opening in a muscle mass. It will allow placement of a retractor with blades having a slight lip on their distal margin to retain the muscle with less risk of muscle escaping and working its way across the operating field.

The present guide will protect both sides of the retractor blade during insertion. It will be inserted through a short separation through the muscle to the bony surface. Opening the guide when the blades are deep will open a space through the muscle without disrupting across muscle fibers. With the muscle maintained medial and lateral to the blades, an opening is maintained to the bony surface. A bladed retractor may be entered in this plane to the bony surface. It will not matter if a portion of the blade is skeletonized or cut out, as the plane will be maintained from one blade member to the other blade member of the guide. As long as there is a full depth portion of the blade member of the guide at either end to rest on the bony surface, the intervening muscle will not be allowed to fall into the surgical field.

Although not shown, a guide of the present invention could be coupled to a retractor by a coupling mechanism, wherein the combined devices are inserted as a single unit, with the guide portions subsequently removed.

To assist in the understanding of the present invention the following list of components and associated numbering found in the drawings is provided herein:

| Number | Component |
|---|---|
| 10, 10' | guide |
| 12, 12' | blade portion |
| 14 | first blade member |
| 16 | second blade member |
| 18 | exterior surface |
| 20 | distal end |
| 22 | proximal end |
| 23 | quarter-rounded tip |
| 24 | handles |
| 26 | extension portions |
| 28 | pivot point |
| 30 | spring mechanism |
| 32 | tip |

-continued

| Number | Component |
|---|---|
| 33 | screw or bolt |
| 34 | front |
| 36 | rear |
| 38 | rounded corners |
| 40 | interior region |
| 42 | slot |
| 44 | shoulder |
| 46 | inner surface |
| 48 | distal end of retractor R |
| 50 | front lateral portion |
| 52 | aperture |
| 54, 54' | guide |
| 56 | first member |
| 58 | second member |
| 60 | side edge |
| 62 | lateral aperture |
| 64 | interior side flange |
| 66 | tapered edges |
| 68 | interior tip flange |
| 70 | retractor tips |
| 72 | projections |
| 74 | grooves |
| 76, 76' | guide |
| 78 | funnel shaped top portion |
| 80 | lower portion |
| A—A | longitudinal axis |
| I | incision |
| θ | blade separation angle (between blades 14, 16) |
| φ | handle separation angle (between blades and extension portion/handle) |
| L | length |
| R | retractor |
| $t_1$ | thickness (of first member 56) |
| $t_2$ | thickness (of second member 58) |
| $T_{db}$ | thickness of distal end of blades 14, 16 |
| $T_{pb}$ | thickness of proximal end of blades 14, 16 |
| $T_{tip}$ | thickness of tip |
| $W_i$ | inside width of members 56, 58 |
| $W_o$ | outside width of members 56, 58 |
| $W_{db}$ | width of distal end of blades 14, 16 |
| $W_{pb}$ | width of proximal end of blades 14, 16 |

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

While various embodiments of the present invention have been described in detail, it will be apparent that further modifications and adaptations of the invention will occur to those skilled in the art. It is to be expressly understood that such modifications and adaptations are within the spirit and scope of the present invention.

What is claimed is:

1. A guide for a retractor, comprising:
a first member and a second member detachably engageable with said first member, each of said first member and said second member having a pair of spaced apart side flanges and a recessed interior surface between said side flanges, wherein a slot is formed upon contacting an inside edge of said first member with a corresponding apposed inside edge of said second member, wherein said first member and said second member include a tip flange with gaps between said side flanges of each member and said tip flange of each member, wherein said slot is adapted for receiving the retractor therein, and wherein said tip flange protrudes inwardly relative to said interior surface and into a portion of the slot.

2. The guide as claimed in claim 1, wherein said first member and said second member include a distal end having tapered edges.

3. The guide as claimed in claim 2, wherein said distal end includes a rounded tip.

4. The guide as claimed in claim 3, wherein said rounded tip is a substantially quarter-rounded tip.

5. The guide as claimed in claim 1, wherein said recessed interior surface has a width of between about 12 to 20 millimeters.

6. The guide as claimed in claim 1, wherein said first member and said second member have a length of between about 25 to 90 millimeters.

7. The guide as claimed in claim 1, wherein said first member and said second member each have a thickness at a distal end of about 1 millimeter.

8. The guide as claimed in claim 1, wherein said slot is substantially V-shaped.

9. The guide as claimed in claim 1, wherein said slot extends from a proximal end of said first member and a proximal end of said second member to a position at or near a distal end of said first member and a distal end of said second member.

10. The guide as claimed in claim 1, wherein apertures are formed at lateral positions of a distal end of said first member and a distal end of said second member upon contacting said tip flange and said inside edge of said first member with the corresponding apposed tip flange and inside edge of said second member.

11. A guide for a retractor, comprising:
   a first member and an apposed detachable second member, each having a length of between about 25 to 90 millimeters;
   each of said members having a distal end and a proximal end, said distal end of said first member and said distal end of said second member each having tapered edges and a thickness of about 1 millimeter;
   each of said distal ends having a substantially quarter-rounded tip which, when paired together, forms a substantially half-rounded end portion or tip;
   each of said members having a pair of spaced apart side flanges and a recessed interior surface between said side flanges, said recessed interior surface having a width of between about 12 to 20 millimeters and having a substantially V-shaped slot, extending from both of said proximal ends to a position at or near both of said distal ends, formed upon contacting an inside edge of said first member with a corresponding apposed inside edge of said second member, said slot adapted for receiving the retractor therein; and
   each of said members having an interior tip flange, raised relative to said interior surface, with gaps between said side flanges of each member and said tip flange of each member, wherein apertures are formed at lateral positions of both of said distal ends upon contacting said interior tip flange and said inside edge of said first member with the apposed interior tip flange and inside edge of said second member.

12. A guide for a retractor, comprising:
   a first member detachably engageable with a second member, each of said first member and said second member having a pair of spaced apart side flanges, a recessed interior surface between said side flanges, and a tip flange, with gaps between said side flanges of each member and said tip flange of each member, and wherein said tip flange protrudes inwardly from said interior surface.

13. The guide as claimed in claim 12, wherein a slot is formed upon contacting an inside edge of said first member with a corresponding apposed inside edge of said second member.

14. The guide as claimed in claim 13, wherein said slot is adapted for receiving the retractor therein.

15. The guide as claimed in claim 13, wherein said slot is substantially V-shaped.

16. The guide as claimed in claim 13, wherein said slot extends from a proximal end of said first member and a proximal end of said second member to a position at or near a distal end of said first member and a distal end of said second member.

17. The guide as claimed in claim 12, wherein said first member and said second member include a distal end having tapered edges.

18. The guide as claimed in claim 17, wherein said distal end includes a rounded tip.

19. The guide as claimed in claim 18, wherein said rounded tip is a substantially quarter-rounded tip.

20. The guide as claimed in claim 12, wherein said recessed interior surface has a width of between about 12 to 20 millimeters.

21. The guide as claimed in claim 12, wherein said first member and said second member have a length of between about 25 to 90 millimeters.

22. The guide as claimed in claim 12, wherein said first member and said second member each have a thickness at a distal end of about 1 millimeter.

23. The guide as claimed in claim 12, wherein apertures are formed at lateral positions of a distal end of said first member and a distal end of said second member upon contacting said tip flange and an inside edge of said first member with a corresponding apposed tip flange and inside edge of said second member.

* * * * *